United States Patent [19]

Beardsley

[11] Patent Number: 5,616,554
[45] Date of Patent: Apr. 1, 1997

[54] IMMUNE-ENHANCING AGENT FOR THERAPEUTIC USE IN IMMUNOCOMPROMISED HOSTS

[76] Inventor: Terry R. Beardsley, 32547 Mesa Lilac Rd., Escondido, Calif. 92026

[21] Appl. No.: 280,781

[22] Filed: Jul. 26, 1994

Related U.S. Application Data

[63] Continuation-in-part of Ser. No. 850,586, Mar. 13, 1992, abandoned.

[51] Int. Cl.$^6$ .................................................. A61K 38/16
[52] U.S. Cl. ............................ 514/8; 514/21; 530/395; 530/397; 530/399
[58] Field of Search ..................... 530/395, 397, 530/837, 854, 399; 514/8, 21

[56] References Cited

U.S. PATENT DOCUMENTS

| | | | |
|---|---|---|---|
| 4,120,951 | 10/1978 | Goldstein | 424/177 |
| 4,571,336 | 2/1986 | Houck et al. | 424/95 |
| 4,716,148 | 12/1987 | Horecker | 514/12 |
| 4,720,482 | 1/1988 | Cantor et al. | 514/2 |
| 4,722,998 | 2/1988 | Cantor et al. | 530/351 |
| 4,814,434 | 3/1989 | Goldfarb | 530/380 |
| 4,904,643 | 2/1990 | Brunetti et al. | 514/21 |
| 4,965,195 | 10/1990 | Namen et al. | 435/69.52 |

FOREIGN PATENT DOCUMENTS 116054  9/1988  WIPO.

OTHER PUBLICATIONS

Ogata, et al. "Thymic Stroma–Derived T Cell Growth Factor (TSTGF) Journal of Immunol." 139:8 pp. 2675–2682, (Oct. 1987).
Waksal, et al. "Induction of T–Cell Differentiation Invitro by Thymus Epithelial Cells" Annals New York Academy of Sciences, pp. 492–498, 1975.
Beardsley, et al. "Induction of T–Cell Maturation by a Cloned Line of Thymic Epithelium (TEPI) Immunology 80:" pp. 6005–6009, (Oct. 1983).
Hays, et al. "Immunologic Effects of Human Thymic Stromal Grafts and Cell Lines" Clin. Immunol and Immunop. 33: pp. 381–390, (1984).
Au Lupin D. et al. "The Prerferential Binding of Immature Thymocytes to a Rat" So Thymus 14(4) Abstract (1989).
Fox, BioTech., vol. 12, p. 128, Feb. 1994.
Meijer et al., Antiviral Res., vol. 18, pp. 215–258, 1992.
Fahey et al., Clin. exp. Immunol., vol. 88, pp. 1–5, 1992.
Martin et al., Cancer Res., vol. 46, pp. 2189–2192, Apr. 1986.
Jain, Scientific American, p. 58, Jul. 1994.
Lane, The New England Jour. of Med., vol. 311 (17), pp. 1099–1103, 1984.
Lane, Annals of Internal Medicine, vol. 103, pp. 714–719, 1985.
Hirsch, The Amer. J. Med., vol. 86 (suppl. 2A), pp. 182–185, 1988.
Osband et al., Immunol. Today, vol. 11(6), pp. 193–195, 1990.
Konrad, "Biological Barrier to Protein Delivery", eds. Audus et al., Plenum Press, pp. 409–437, 1993.
Curti, Crit. Rev. in Oncology/Hematology, vol. 14, pp. 29–39, 1993.
Wedner, Basic & Clin Immunol., Eds Stiles et al., 7th Edition, Appleton & Lange, Chap 34, 1991.

*Primary Examiner*—Chhaya D. Sayala
*Attorney, Agent, or Firm*—Knobbe, Martens, Olson & Bear

[57] ABSTRACT

The present invention relates generally to the fields of immunology and molecular biology, and particularly to a thymus-derived factor which stimulates, enhances or regulates cell-mediated immune responsiveness. In one embodiment, the factor is a substantially homogeneous immune potentiator which stimulates mature T lymphocytes and thus enhances the response of animals, especially mammalian organisms, to infectious agents and to malignancies.

24 Claims, 8 Drawing Sheets

* PERCENT ABOVE UNTREATED CONTROLS
PIT-POST INITIATION OF TREATMENT

FIG. 6

IMMUNE-ENHANCING AGENT FOR THERAPEUTIC USE IN IMMUNOCOMPROMISED HOSTS

CROSS REFERENCE TO RELATED APPLICATIONS

This application is a continuation-in-part of U.S. Ser. No. 07/850,586, filed Mar. 13, 1992 now abondoned.

FIELD OF THE INVENTION

The present invention relates generally to the field of immunology, and particularly to a polypeptide factor which stimulates or regulates the proliferation and differentiation of lymphocyte and other hematopoietic progenitors and which enhances the response of animals to infectious agents and to malignancies.

BACKGROUND OF THE INVENTION

The function of the thymus gland, which lies just beneath the breast bone, was only first revealed in 1960. Prior to that time, the thymus was thought to be of little importance since in adults it is almost non-existent because of rapid atrophy after adolescence. As was the case with other organs (e.g., the pancreas), the function of the thymus was suggested by observing the effect of its removal in young animals. When pre-adolescent animals are thymectomized, they experience a profound "wasting disease" which is characterized by a variety of maladies, including increased incidence of infection and cancer, failure to grow, allergies and neuromuscular paralysis. The greater susceptibility to infection and cancer was shown to be directly attributable to a dramatic decrease in peripheral blood lymphocytes, and could be prevented by rearing the animal in a germ-free environment. However, the other symptoms of thymectomy were not completed abrogated by this approach.

In 1964, it was demonstrated that hormone-like factors from thymus tissue could prevent many of the manifestations of "wasting disease," thus suggesting that the thymus produces substances important in the development of immunity. The relationship of this observation to the other "wasting disease" symptoms was not well understood at that time, however.

B and T lymphocytes are the primary effector cells of the immune response. Both cell classes are considered to derive ultimately from hematopoietic stem cells in the mammalian bone marrow, via progenitor or precursor cells representing distinguishable stages in the differentiation of each class. B lymphocytes, or B cells, are the precursors of circulating antibody-secreting plasma cells. Mature B cells, which are characterized by expression of surface-bound immunoglobulin capable of binding specific antigens, derive from hematopoietic stem cells via an intermediary cell class known as pre-B cells. Mature T cells develop principally in the thymus, presumably from an as yet unidentified precursor cell which migrates from the bone marrow to the thymus at an early stage of T lymphocyte development.

It was not until 1971 that it was discovered that the thymus-derived lymphocytes (T cells) regulated the reactivity of bone marrow-derived antibody-producing lymphocytes (B cells). The latter are involved in the pathogenesis of many autoimmune-type diseases, i.e., those involving the body's reactivity to its own cells or tissues. Examples of such diseases include arthritis, multiple sclerosis, muscular dystrophy, lupus erythematosus, and quite possibly juvenile onset diabetes. Many of the problems associated with "wasting disease" in thymectomized animals are similar to "autoimmune-type" disease. In general, when the thymus gland fails to function properly, T cells, which control the immune response, are defective or absent and the system breaks down.

After the discovery that the thymus was producing a hormone-like factor, several groups of scientists began trying to extract and purify the material from thymus glands, or from serum, in much the same manner that insulin was prepared for therapeutic use in diabetes. The difficulty is that the thymus produces very small quantities of the hormone or hormones. Thus, one requires large amounts of calf thymus or several liters of serum to biochemically extract small amounts of active material. Success has been very limited with this approach.

Very little is known about regulatory factors involved in B and T cell lymphogenesis. In particular, all the factors or conditions required for commitment and expansion of the B and T cell lineages have not yet been defined, albeit it is now known that one or more thymic factors or hormones are produced by the epithelial cells of the thymus gland. (See, e.g., Waksal, et al., *Ann. N.Y. Acad. Sci.* 249: 493 (1975).) While the ideal approach for studying these factors or hormones would be to isolate these cells from fresh thymic tissue and grow them in vitro, epithelial cells have been extremely difficult to maintain in continuous culture in the laboratory.

Recently, this technical barrier has been overcome, with the presently-disclosed establishment of cloned lines of thymic epithelial cells of feline, canine, bovine and human origin. Earlier efforts to establish a cloned cell line of murine origin laid some of the procedural groundwork for the present invention. (See Beardsley, et al., *PNAS* 80: 6005 (1983), and Hays & Beardsley, *Clin. Immunol. Immunopath.* 33: 381 (1984), which are incorporated herein by reference). The present disclosure demonstrates that the thymic epithelial cell lines of the present invention are, in fact, producing factors having activity similar but not identical to substances previously obtained by the difficult and labor-intensive procedure of extracting thymic substances from calf thymus; however, the presently-disclosed factor is in a much purer and more homogeneous form, is produced in greater quantities and has a different and distinct mechanism of action.

The primary activity of the cloned thymic epithelial cell factors produced according to the presently disclosed method has been shown to have the capacity to augment the immune responses of both immature and mature T cells. This factor, which shall be referred to herein as T4 immune stimulating factor ("TISF"), is being further purified and characterized biochemically. Also, in vivo studies have been initiated to determine the efficacy of TISF in enhancing the response of animals to infectious agents and to malignant cells.

Although much of the work done to date has focused on the murine and canine models, the implications and applications to other animals, e.g., felines, bovine species, and especially to humans, have been shown to be equally relevant. As disclosed herein, the difficult step of establishing a human epithelial cell line has also been accomplished successfully. One immediate goal is to apply the various aspects of the present invention, especially TISF, to produce an effective immune potentiator and/or therapeutic agent for the treatment of immunologically-related disease and to produce agents useful in immunization against etiologic agents of disease.

SUMMARY OF THE INVENTION

In one embodiment of the present invention, there is provided a substantially homogeneous thymus-derived factor expressed by a cloned thymic epithelial cell line, having a molecular weight of about 50,000 daltons, an isoelectric point of about 6.5, and capable of inducing or enhancing cell-mediated immune responsiveness of mature T-cells in mammalian organisms. In an alternative embodiment, the factor comprises one or more polypeptides substantially free of any additional endogenous materials. Preferably, the factor is of feline, canine or bovine origin; most preferably, it is of human origin. In another variation, the factor has the ability to enhance the response of animals to infectious agents.

In another embodiment, a thymus-derived factor according to the present invention has the ability to enhance the response of mammalian organisms to malignant cells. In alternative variations, the mammalian organisms are felines or canines; in preferred embodiments, the mammals are humans.

The present invention also discloses a composition comprising an effective, immune-responsiveness-enhancing amount of thymus-derived factor incorporated in a pharmaceutically acceptable carrier or excipient. In one alternative embodiment, the composition is capable of providing therapeutic benefits in immunocompromised mammalian organisms. Compositions according to the present invention may be provided in a form suitable for parenteral administration, intraperitoneal administration, topical administration or oral administration.

In other embodiments, methods for treating infections in a mammalian organism comprising administering to the organism an effective amount of thymic factor or composition containing the factor is disclosed. In other variations, the infection is caused by a virus. Preferably, the virus is a retrovirus, Feline Immunodeficiency Virus, rabies virus, distemper virus or Human Immunodeficiency Virus. Advantageously, the mammalian organism is either a feline or canine; most advantageously the organism is a human.

In other variations, the compound is administered parenterally, intraperitoneally, after being incorporated within liposomes, topically or orally.

DETAILED DESCRIPTION OF THE INVENTION

As used in the present disclosure, "TISF" refers to a mammalian polypeptide or mixture of polypeptides which are capable of stimulating or regulating the proliferation and differentiation of lymphocyte and other hematopoietic progenitors, including T cell precursors. TISF has its greatest effect in enhancing the response of mature T lymphocytes to infectious agents and to malignant cells.

The primary criterion of effectiveness of the derived factor is its ability to induce immune function in a population of cells which do not function without that induction. Thymocytes are comprised of immature cells which are non-functional and mature T cells which can be stimulated to function against various agents such as viruses and tumors. Originally, this immature cell population was used to test the factor from thymic epithelial cell cultures. As documented in Beardsley, et al., *PNAS* 80: 6005 (1983), the murine thymic cell factor can induce a very substantial immune response in a population of cells that are normally unresponsive. While TISF has a slight but recognizable stimulatory effect on these immature cells, its primary action is directed toward the mature T lymphocyte, resulting in increased viral or tumor immunity. We have distinguished TISF from IL-2 or IL-1, which can have similar, but less dramatic effects. The major difference is that thymocytes only need to be pulsed with TISF for 24 hours, whereas IL-2 must be present throughout the 5day induction phase of the response. TISF has as the primary target of its stimulatory action the unresponsive mature T lymphocyte.

Figure 1A:
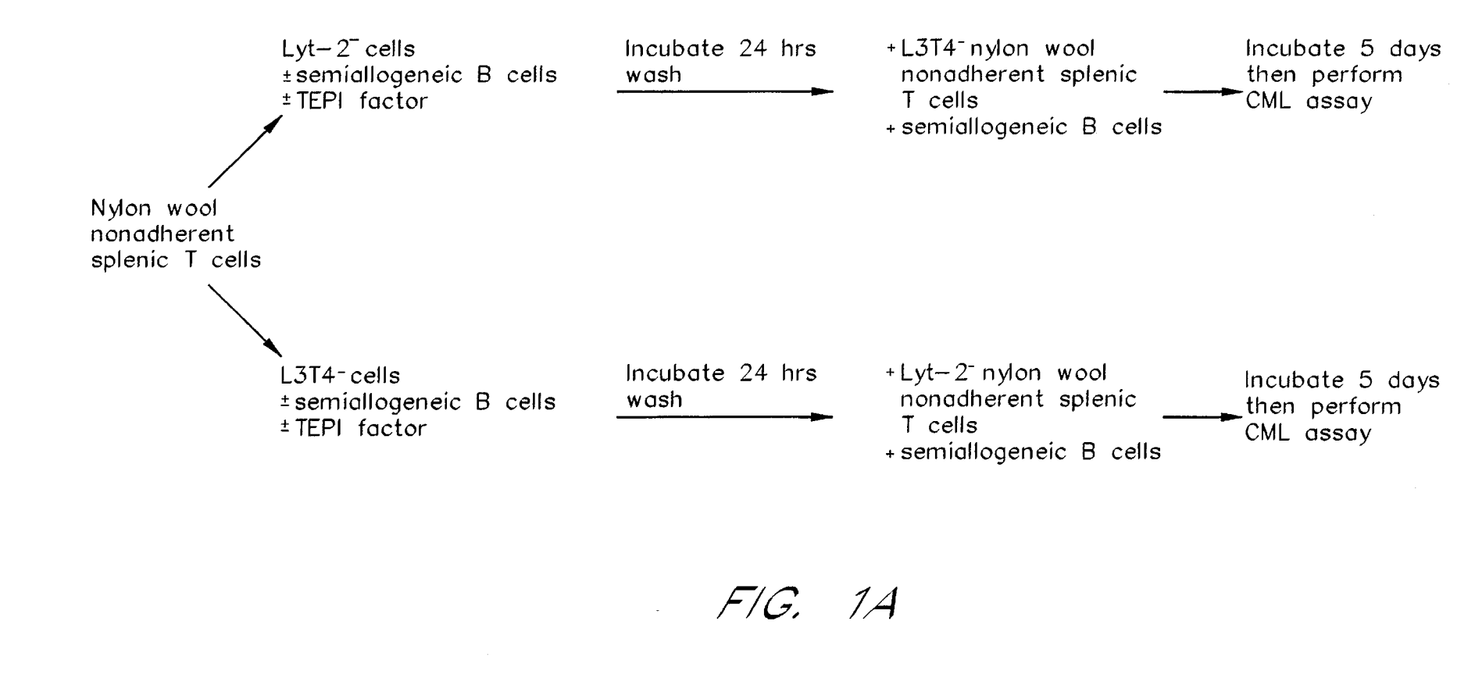
FIG. 1A illustrates the isolation of LYT-2 negative and L3T4 negative cell populations.
Figure 1B:
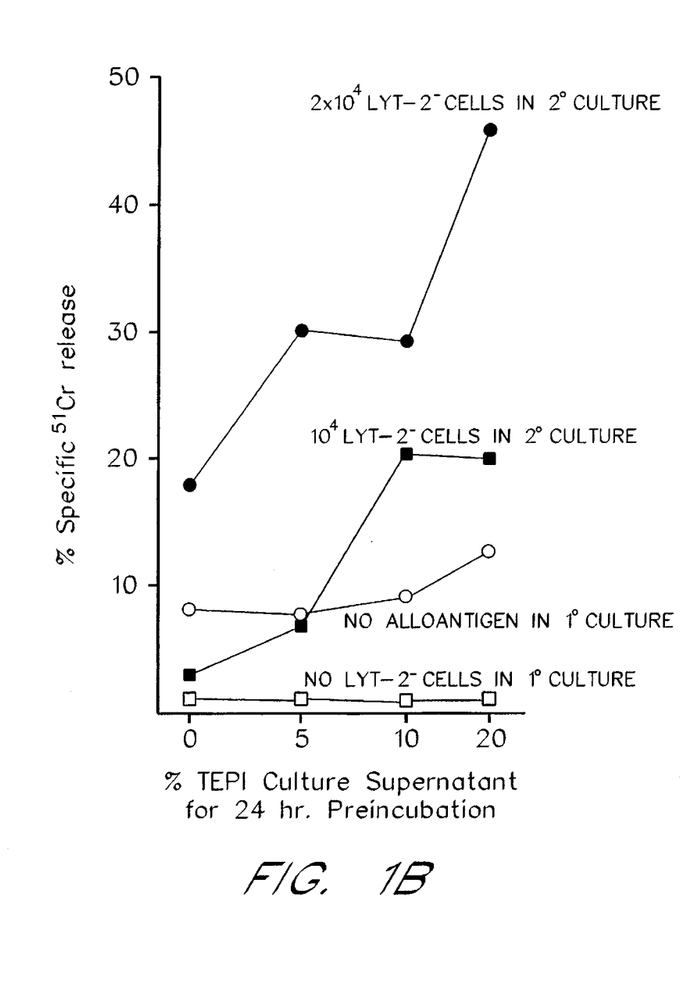
FIG. 1B illustrates the effect of TISF on the LYT-2 negative population.
Figure 1C:
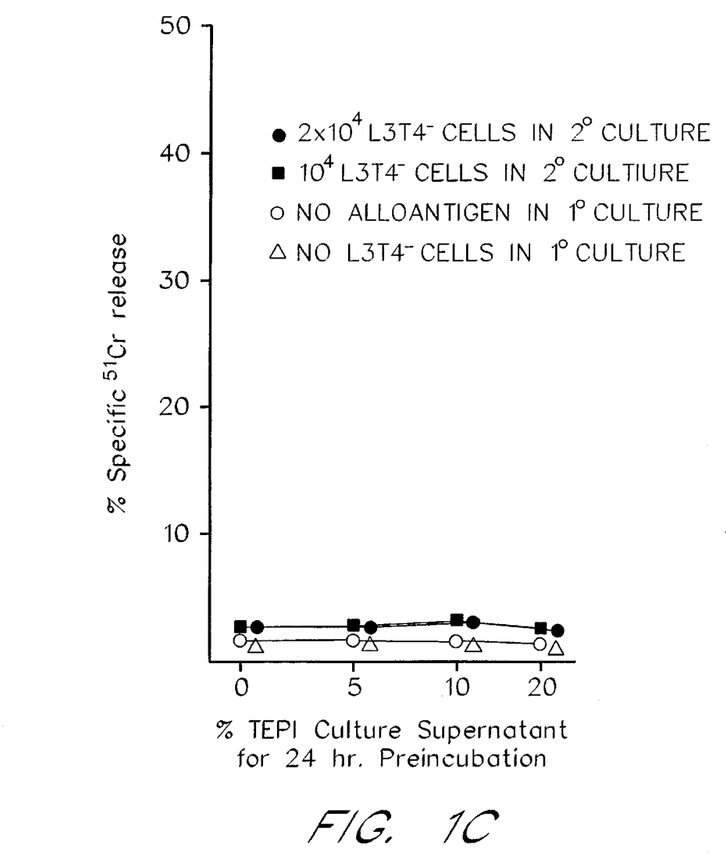
FIG. 1C illustrates the lack of activity in cultures without L3T4 positive helper cells.

It has now been demonstrated that TISF is promoting the response of a helper cell population. FIG. 1B demonstrates that TISF is affecting the LYT-2 negative population. Conversely, cultures devoid of L3T4 positive helper cells (FIG. 1C) have no activity.

Figure 2A:
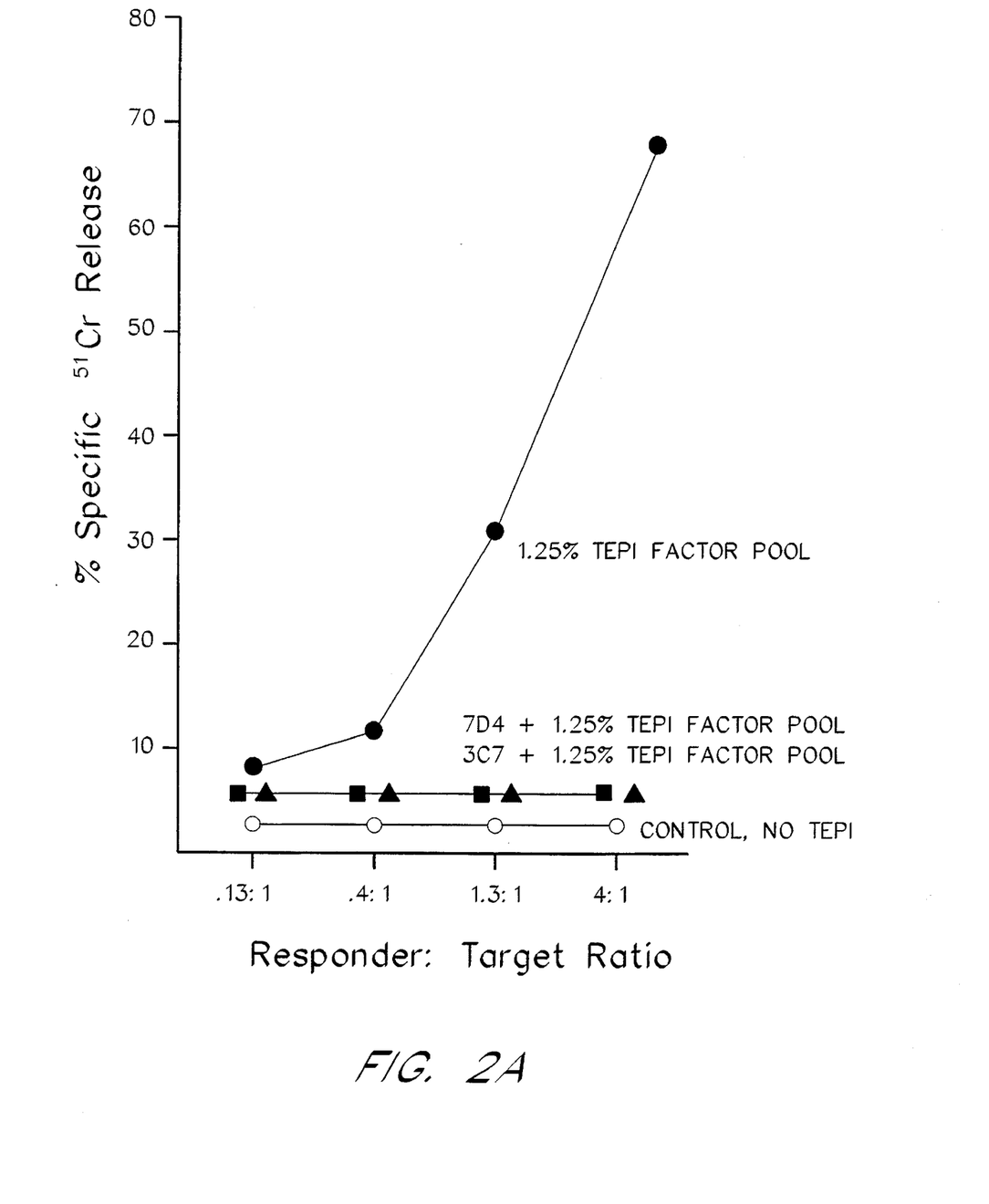
FIG. 2A illustrates blocking of TISF enhancement of cytotoxic killer activity by antibody directed against the IL2 receptor (7D4 or 3C7).
Figure 2B:
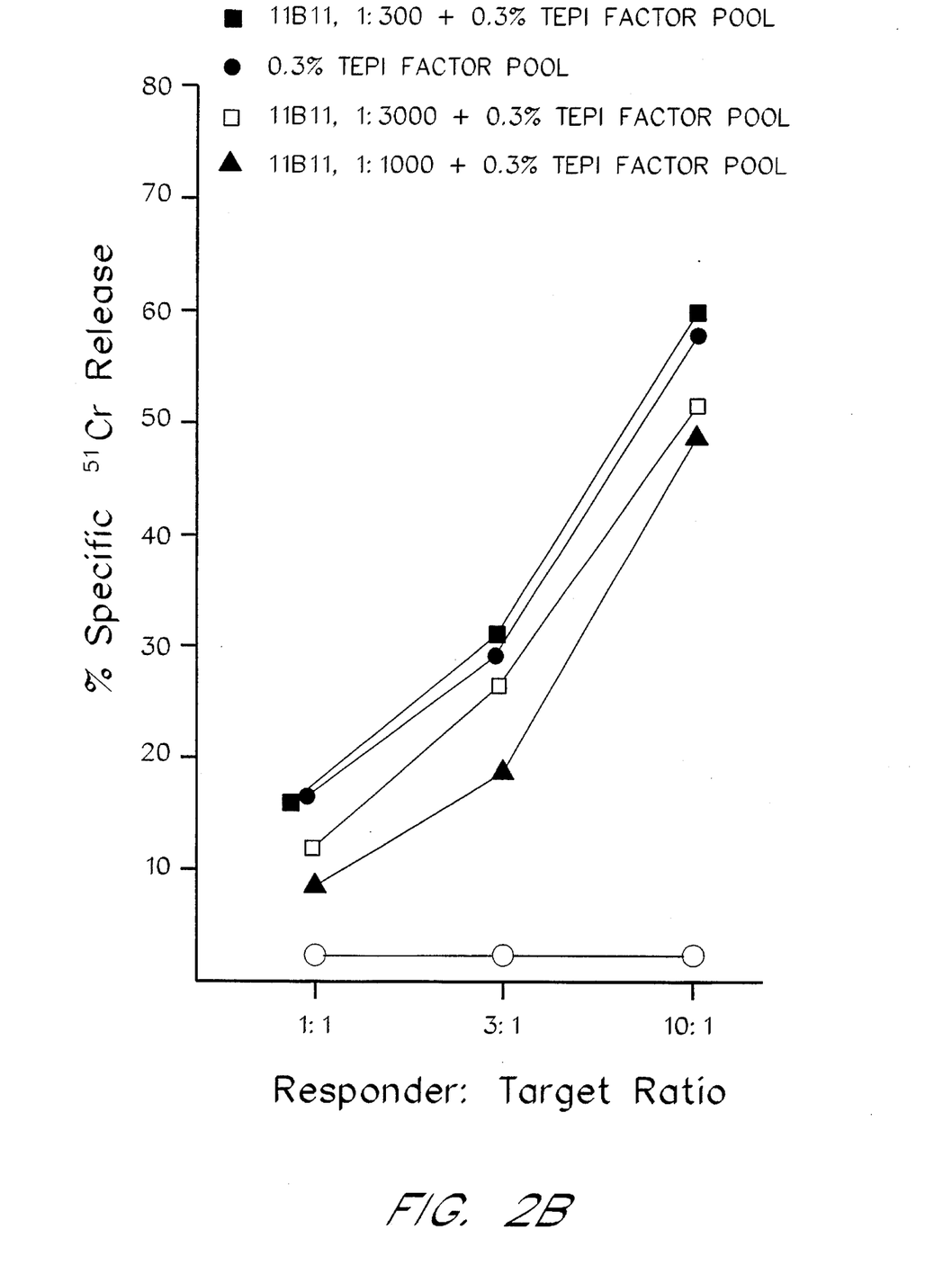
FIG. 2B illustrates that irrelevant antibodies lack a blocking effect.

TISF can greatly enhance or potentiate both antibody-mediated or killer cell responses against infectious agents and/or cancer via its effect on IL-2 producing cells. The tremendous effect of TISF has been shown to be due to its ability to stimulate IL-2 production. This is shown in FIG. 2A by the blocking of TISF enhancement of cytotoxic killer activity by antibody directed against the IL-2 receptor (7D4 or 3C7). Irrelevant antibodies have no blocking effect (FIG. 2B). From a therapeutic standpoint, it makes sense to recruit the helper cells to make IL-2 at the site where they are required, rather than inject a bolus of IL-2 which is rapidly diluted and degraded in body fluid.

Several companies have attempted to demonstrate the effectiveness of IL-2, both as a therapeutic and an adjuvant. The problems are at least two-fold. First, IL-2 is a local, short-acting cytokine. To achieve physiologic levels at the desired site, i.e., a tumor mass, unnaturally large doses must be administered. Thus, the likelihood of the patient suffering from side-effects is dramatically increased. Second, IL-2 must be present continuously for at least five days in order to induce an effective response.

From a practical as well as an economic point of view, IL-2 therapy is logistically difficult and very expensive. Twice-daily injections of IL-2 over a period of five days in a hospital setting would cost over $1,000 just for the drug alone.

In contrast, a substance similar to that which we call TISF is normally present in the blood in physiologically measurable levels, except in certain disease states. Its mode of action is widespread on cells of the immune system throughout the body. Since it is a normal constituent in the circulation, few, if any, side-effects would be expected. However, the greatest advantage is that a single injection of TISF has long-lasting effects and could be self-administered much like insulin, only less frequently. Therefore, patient and physician convenience, plus the relatively reduced cost, would enhance clinical acceptance.

TISF may be subjected to a series of purification steps in order to obtain an extract with higher degrees of purity. For example, in Table 1, the use of purification methods such as an AX 300 column (anion exchange beads) or a CM 300 column (cation exchange beads) is illustrated. An overall TISF purification of greater than 200 fold was obtained from a crude thymic cell culture supernatant.

homogeneous fraction with a major band flanked by two minor bands. Sequence analysis of the TISF fractions is expected to confirm the homogeneity of the fraction produced by the cloned thymic cell lines disclosed herein.

It has been determined that TISF is not any of the previously described cytokines. As previously discussed, TISF is not IL-1 or IL-2. Further testing has also demonstrated that TISF is not IL-4 (see Table 2). This was determined by incubating natural killer (NK) cells with either IL-4 or TISF purified from the culture supernatant and measuring the incorporation of $[^{125}I]$-deoxyuridine into RNA. As the Table indicates, IL-4 treatment resulted in a significant increase in incorporation of the label, whereas TISF treatment had no effect.

TABLE I

Purification of TISF factor.

| Material | Volume (ml) | Protein (μg/ml) | Total Protein | Units /ml[a] | Total Units | % Recovery | Specific Activity | Fold-Purification |
|---|---|---|---|---|---|---|---|---|
| Crude SN[b] | 400 | 50 | 20[c] | 10 | 4000 | 100 | 200 | 1 |
| AX 300 | 10 | 100 | 1[d] | 200 | 2000 | 50 | 2,000 | 10 |
| CM 300 | 5 | 12 | 0.06 | 200 | 1000 | 50 | 16,700 | 83 |
| C4[e] | 2 | 4.5 | 0.009 | 100 | 400 | 20 | 44,400 | 222 |

[a]The number of units/ml of activity is functionally defined as the inverse of the maximum dilution of sample which still yields at least 90% of the maximal stimulation of the CTL (cytotoxic T lymphocyte) response to alloantigen. Such a definition insured a strong signal and provided excellent consistency between assays.
[b]Initial volume of TISF culture supernatant (SN) collected under serum free conditions.
[c]Protein concentration was determined by bradford protein assay (BioRad Laboratories, Richmond, CA).
[d]Protein concentration was determined from HPLC optical density trace using known standards.
[e]Material from the AX 300 column that has not been fractionated on the CM 300 column.

TABLE II

Differences between unfractionated TISF SN and IL-4

| Factor | No Il-4 Addition | Additional of IL-4[A] | | |
| | | 3 U/ml | 1 U/ml | 0.3 U/ml |
|---|---|---|---|---|
| None TISF SN | 160 (141–181)[b] | 5278 (4696–5932) | 3928 (3538–4361) | 2212 (2158–2300) |
| 10% | 171 (161–182) | 4498 (3296–6138) | 2823 (2803–2842) | 1876 (1850–1903) |
| 3% | 172 (145–204) | 4186 (3735–6138) | 3163 (3086–3243) | 2103 (2049–2159) |
| 1% | 203 (162–255) | 4728 (4612–4847) | 3267 (3080–3464) | 2169 (2002–2350) |
| 0.3% | 159 (143–177) | 4449 (4255–4652) | 3417 (3234–3611) | 2425 (2362–2546) |

[a]Purified IL-4
[b]Results are expressed as mean $^{125}$IUdR cpm/culture, followed by the ±1 standard deviation range in parentheses. cultures contained $5 \times 10^3$ NK cells per cell.

Polyacrylamide gel analysis under non-reducing conditions demonstrates that TISF appears as a substantially In addition, we have determined that TISF contains no IL-5 or granulocyte-macrophage colony stimulating factor (GM-CSF), as shown in Table 3. The fact that TISF does not have any direct stimulatory activity for B cells would suggest that it is also not IL-3, IL-6 or IL-7. Further purification and genetic cloning are in progress to specifically identify the detailed molecular characteristics of TISF.

limiting dilution at one cell per well was less successful than "seeding" the wells with three or four individual cells, which tended to grow to confluency. Single cells plated in limiting dilution were more likely to grow to confluency if epidermal

TABLE III

TISF SN contains no IL-5 or GM-CSF activity

| Factor added | IL-5 Assay[a] No IL-5 Addition | GM-CSF Assay[b] | | |
|---|---|---|---|---|
| | | 3.0% addition of purified IL-5[c] | No GM-CSF Addition | Addition of[d] 1 U/ml GM-CSF |
| None Unfractionated TISF SN | 467 (372–588)[e] | 3532 (3336–3739) | 6 (3–12)[e] | 830 (779–884) |
| 10% | 212 (201–224) | 2193 (1976–2434) | 24 (19–31) | 688 (661–717) |
| 3% | 267 (251–284) | 3154 (2556–3890) | 24 (19–30) | 674 (630–722) |
| 1% | 236 (271–258) | 3392 (2678–4295) | 35 (34–36) | 668 (630–708) |
| Partially purified | | | | |
| 3% | 300 (256–351) | 3003 (2546–3542) | 17 (8–33) | 834 (804–866) |

[a]IL-5 activity was determined by using the B cell lymphoma BCL1 (ATCC, Rockville, MD).
[b]GM-CSF activity was determined using the DA-3 line (ATCC, Rockville, MD).
[c]IL-5 was purified from the culture SN of the D10.G4.1 Th2 cell line as described by McKenzie et al. (J. Immunol. 139: 2661 (1987). The preparation used in these experiments contained approximately 500 units/ml.
[d]Purified GM-CSF purchased from Genzyme Corp. (Cambridge, Mass.).
[e]The results are expressed as mean $^{125}$IUdR cpm/culture, followed by the 95% confidence interval in parentheses.
[f]Pooled active fractions from the Sepharose S cation exchange column (Pharmacia, Piscataway, NJ), as detailed in the product manual.

A cloned cell line of thymic cells may be established as described herein. For example, in accordance with the present invention, thymic stromal cells of feline origin were established as a continuously replicating, cloned cell line, according to the method described in Beardsley, et al., *PNAS* 80: 6005 (1983), which is incorporated herein by reference. A selection process was used to isolate a cell line producing homogenous TISF.

The same technique has been employed to establish cloned thymic epithelial cell lines from thymic tissue removed from juvenile dogs and calves and from human thymic remnants removed from children undergoing cardiac surgery.

Preparation of Thymic Cell Lines

Briefly, the procedure for reproducibly obtaining the cell lines of the present invention is as follows. Thymus tissue was removed aseptically under general anesthesia. The tissue removed was placed immediately into tissue culture. A primary culture of about $1 \times 10^8$ thymocytes was established in a 60 mm Petri dish in 5 ml of DMEM and 20% fetal calf serum. After about 48 hours, the thymocytes were gently washed away and the scattered few adherent cells were fed with 50% fresh DMEM containing 20% fetal calf serum and 50% conditioned medium, obtained after centrifugation of the thymocytes. Primary cultures containing a variety of cell types were maintained by weekly feeding with a similar 50:50 mixture of fresh and conditioned medium. After about four weeks, several isolated colonies of epithelial-like cells covered the plate. At this time, a secondary culture was made by transfer of several of these colonies scraped from the primary culture. Growth tended to be slow until the third subculture, when cells began to form a monolayer within 4–5 days. Cloning of the cells by limiting dilution at one cell per well was less successful than "seeding" the wells with three or four individual cells, which tended to grow to confluency. Single cells plated in limiting dilution were more likely to grow to confluency if epidermal growth factor was added at 6 ng/ml to wells containing single cells.

Clones exhibiting epithelial-like morphology were grown out and the supernatants tested for their ability to enhance alloreactivity in whole thymocyte populations. Supernatants from confluent thymus-derived cultures were tested for their capacity to promote thymocyte functional activity. For example, one such method involved testing the ability of the supernatant to augment the cytotoxic T lymphocyte (CTL) response of thymocytes to allogenic major histocompatibility complex (MHC) antigen. Supernatants exhibiting the capacity to induce or enhance cell-mediated immune responsiveness were preferentially selected for testing and further purification.

Cells are preferably propagated in Dulbecco's minimal essential medium (DMEM) high glucose formulation (Irvine Scientific, Santa Ana, Calif.), supplemented with L-glutamine and one or more appropriate antibiotics (i.e., penicillin G 100 IU/ml; streptomycin 100 µg/ml). The medium may further be supplemented with 1–10% fetal bovine serum or proven serum-free substitute (e.g. Serxtend™, Irvine Scientific, Santa Ana, Calif.). Maintenance medium is made as noted above, without the serum.

The cell cultures may be propagated and maintained according to known methods. Those used in the present invention were propagated in an artificial capillary bed (hollow fiber bioreactor) according to the method described in Knazek and Gullino, *Tissue Culture Methods and Applications*, Chp. 7, p. 321 et seq., Kruse and Patterson, eds., Academic Press, N.Y., 1973, which is incorporated herein by reference. Another means of propagating and maintaining a cell line is via weekly passage and growth in DMEM and 10% fetal calf serum. The growth medium may be removed from 5-day cultures and replaced with serum-free DMEM for 24 hours. The 24-hour supernatant is useful as the source of thymic factor. A cloned feline cell line in accordance with the present invention is permanently maintained by the inventor under the designation Fe2F, a canine cell line is permanently maintained under the designation Ca-9, a bovine cell line is permanently maintained under the designation TF4, and a human cell line is permanently maintained under the designation HU1.

In a preferred embodiment, as illustrated by the following examples, thymic stromal cell-derived TISF is produced by type II epithelial cells. Cloned cells from a primary culture of thymic tissue are selected initially on the basis of morphology (sere Beardsley, et al., *PNAS* 80: 6005 (1983), for example, for a description of desired morphological characteristics). Secondarily, cloned lines are selected on the basis of production of TISF, as determined by known in vivo or in vitro bioassay procedures. Purity of the cultures is maintained via regular monitoring for invasive organisms including viruses, bacteria, and fungi.

Purification of Thymic Factor

The TISF is a strongly cationic glycoprotein, and may be purified with cation exchange resin. Purification of the supernatants selected (see, e.g., Table I) produced a substantially homogeneous factor (TISF). Using known assay techniques as described above, it is now apparent that the effective component of TISF is comprised of at least one polypeptide substantially free of additional endogenous materials. The human, feline, canine and bovine TISF of the present invention are substantially homogeneous 50 kDa glycoproteins with isoelectric points of 6.5.

The amino acid composition of TISF is unlike that of any known cytokine or thymic peptide. The amino acid composition of bovine TISF was determined by conventional methods known to those of skill in the art and is as follows.

Asparagine/Aspartate—8.8%; Threonine—3.5%; Serine—14.7%; Glutamine/Glutamate—13.3%; Proline—2.2%; Glycine—25.7%; Alanine—6.1%; Valine—4.3%; Isoleucine—3.4%; Leucine—6.3%; Tyrosine—2.3%; Phenylalanine—2.6%; Histidine—2.2%; Lysine—4.7%

TISF was purified on a larger scale according to the following protocol. Seed cultures of Fe2F, Ca-9, TF4, or HU1 were removed from frozen culture and grown in 25 Cm² tissue culture dishes in supplemented DMEM. After 14–21 days incubation at 36° C., cultures were used to inoculate a hollow fiber bioreactor. 5×10⁶–10⁸ cells were inoculated into the extracapillary space (ECS) of an artificial capillary bed. One liter of DMEM supplemented with L-glutamine and antibiotics (e.g., penicillin G, 100 U/ml or streptomycin, 100 µg/ml) was circulated in the capillary bed. After seeding the reactor and allowing for adaptation (3–6 weeks), the concentration of fetal bovine serum was gradually decreased to approximately 0.5% in the media. Cultures were fed every other day by replacement of the circulating capillary bed media. Product was harvested from the media removed from the ECS of the reactor. In one procedure, for example, 500–1000 ml media was exchanged in the capillary bed and 30 ml in the ECS.

When one liter of ECS fluid was collected, it was clarified by centrifugation. The clarified material was passed through a sterile chromatography column which contained a strong cation exchange resin (Sepharose S, Pharmacia) with a high affinity for the product at low salt concentrations. The column was eluted with increasing salt concentrations to 0.5M, whereby all extraneous material was removed from the column. The strongly cationic product was then eluted with sterile 2M buffered saline. The material was then diluted with sterile water to the concentration of normal saline. The final product has a preferable concentration of about 1 µg/ml. The product may be lyophilized, if desired, for long term storage.

Administration of TISF

TISF may be administered to an immunocompromised animal or one with an immature immune system via various means, including parenteral, oral, topical and intraperitoneal administration. A minimally effective dosage of TISF was determined to be about 1 µg/kg of the recipient's body weight. In many of the examples that follow, the dosage range was from about 0.1 µg to about 1 µg TISF per administration; preferably, at least about 5 µg TISF per kilogram of host body weight is administered to the animal with an upper limit of about 500 µg/kg. TISF may efficaciously be administered alone, in combination with another immune potentiator, or incorporated in a pharmaceutically acceptable carrier or excipient.

For treatment of feline immunodeficiency virus infection, cats may advantageously be injected with 1 ml of the above product per week. for treatment of canine or human infections, increased doses are used to adjust for their increased mass and body surface area.

The invention can be better understood by way of the following examples which are representative of the preferred embodiments thereof, but which are not to be construed as limiting the scope of the invention.

EXAMPLE I

Figure 3:
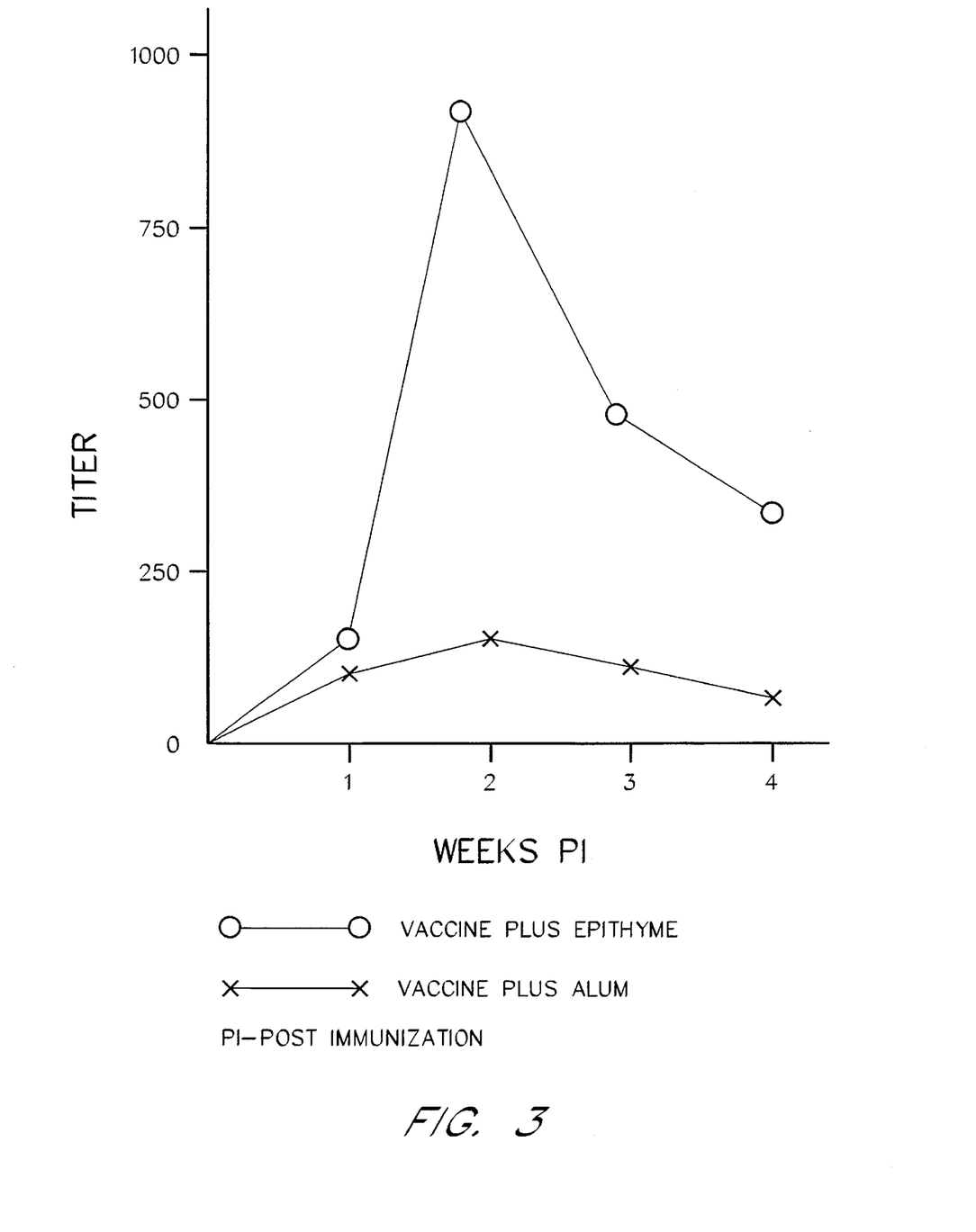
FIG. 3 illustrates TISF enhancement of antibody responses to rabies virus.

In the canine model, TISF has been demonstrated to enhance antibody responses to rabies virus at least 5-fold. In FIG. 3, the effect of canine TISF ("Epithyme™") on anti-rabies virus antibody titers in dogs vaccinated with killed rabies virus vaccine is illustrated. For example, in the control group, which was vaccinated with killed rabies virus vaccine plus alum, anti-rabies virus antibody titers peaked within two weeks at a level well below 250. It is thus striking to observe the results from the experimental group, vaccinated with killed virus and TISF ("Epithyme™"). The animals in the experimental group demonstrated persistent, increased titers which peaked about two weeks postimmunization, at a level exceeding 750. Not only was immune responsiveness enhanced, survival of the animals was enhanced and increased in duration by the administration of TISF.

When one considers the fact that our protocol was preliminary and had not yet been optimized, this result is even more significant. Also, as these tests were performed using semi-purified material, it is expected that use of more highly purified material will show TISF to be even more potent when testing protocols are optimized.

EXAMPLE II

In a second model used to test the efficacy of TISF, canines were immunized with a virulent distemper virus adjuvanted with either alum or canine TISF. Distemper viruses are known to have immunosuppressive effects. The animals were then challenged with a virulent strain of distemper virus to assess protection. A third group—namely, a control, unvaccinated group—was also included in the study.

Figure 4:
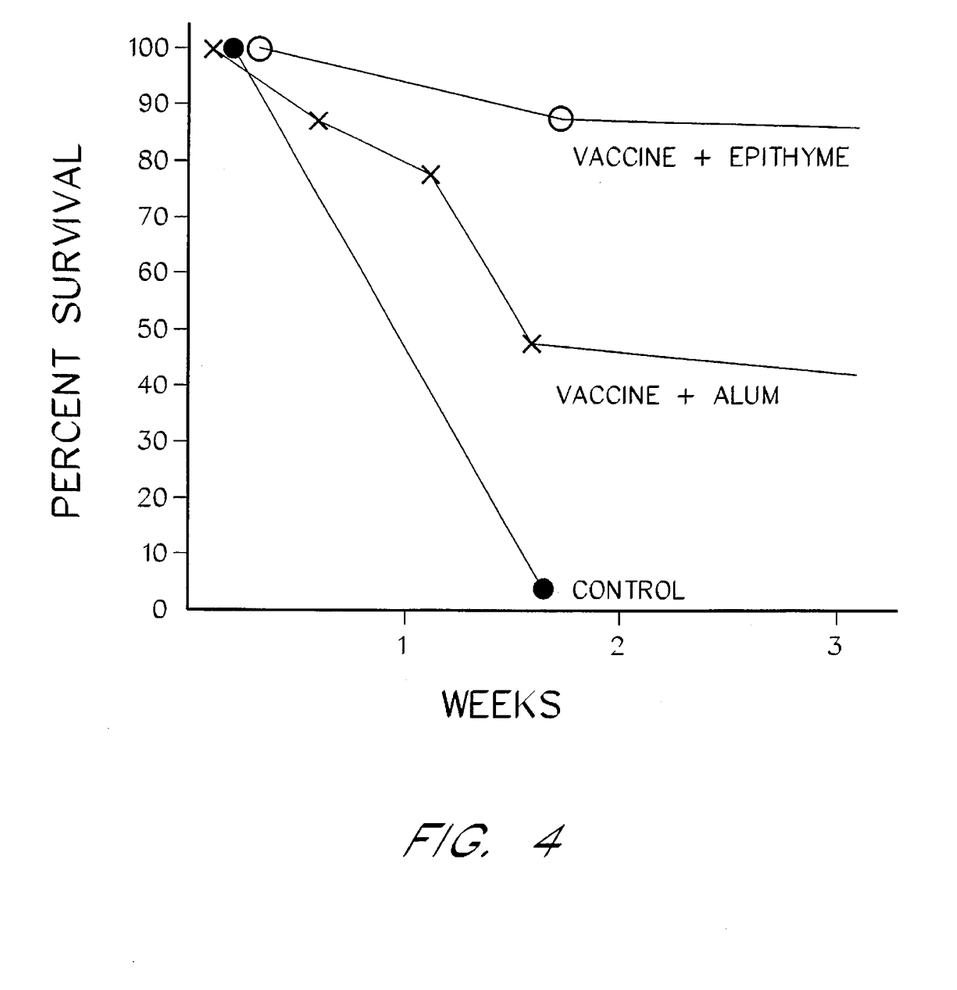
FIG. 4 illustrates survival data in a model used to test the efficacy of TISF in dogs immunized with distemper virus adjuvanted with either alum or TISF and then challenged with a virulent strain of distemper virus.

The survival data are indicated in FIG. 4, which compares the survival rate of the three groups subsequent to canine distemper virus challenge. Clearly, the survival rate of the animals to which vaccine and TISF were administered is about double that of animals receiving vaccine adjuvanted with alum. Since cell-mediated immune (CMI) responses are deemed to be important in the protection against distemper, it is anticipated that measurement of lymphocyte proliferation response will correlate well with survival rates in the vaccine-plus-TISF group.

EXAMPLE III

The beneficial in vivo effects of TISF have more recently been demonstrated in relation to a third viral disease, i.e., influenza. It is generally believed that organisms are more susceptible to influenza ("flu") infection if they are already experiencing some immunosuppressive condition—e.g., stress or chemotherapy—albeit the flu infection itself is also immunosuppressive.

In a mouse model of infection, the primary protection, as in humans, is provided by increased antibody titers to the hemagglutinin antigen (HA). In a primary response to flu, HA titers were enhanced 8-fold. Titers were 1:20 in young mice inoculated with virus alone, and were 1:160 in mice receiving viral inoculations plus TISF. The cell-mediated response to influenza virus is critical for the recovery from the infection. This is important because the CMI is directed to a highly conserved, non-structural gene product expressed on infected cells that is common to all known influenza A strains. Therefore, if one becomes infected with influenza due to the genetic variability of the HA molecule, a more vigorous CMI response could very well shorten the duration of the illness, since "memory" CMI would be cross-reactive to all flu strains.

Figure 5:
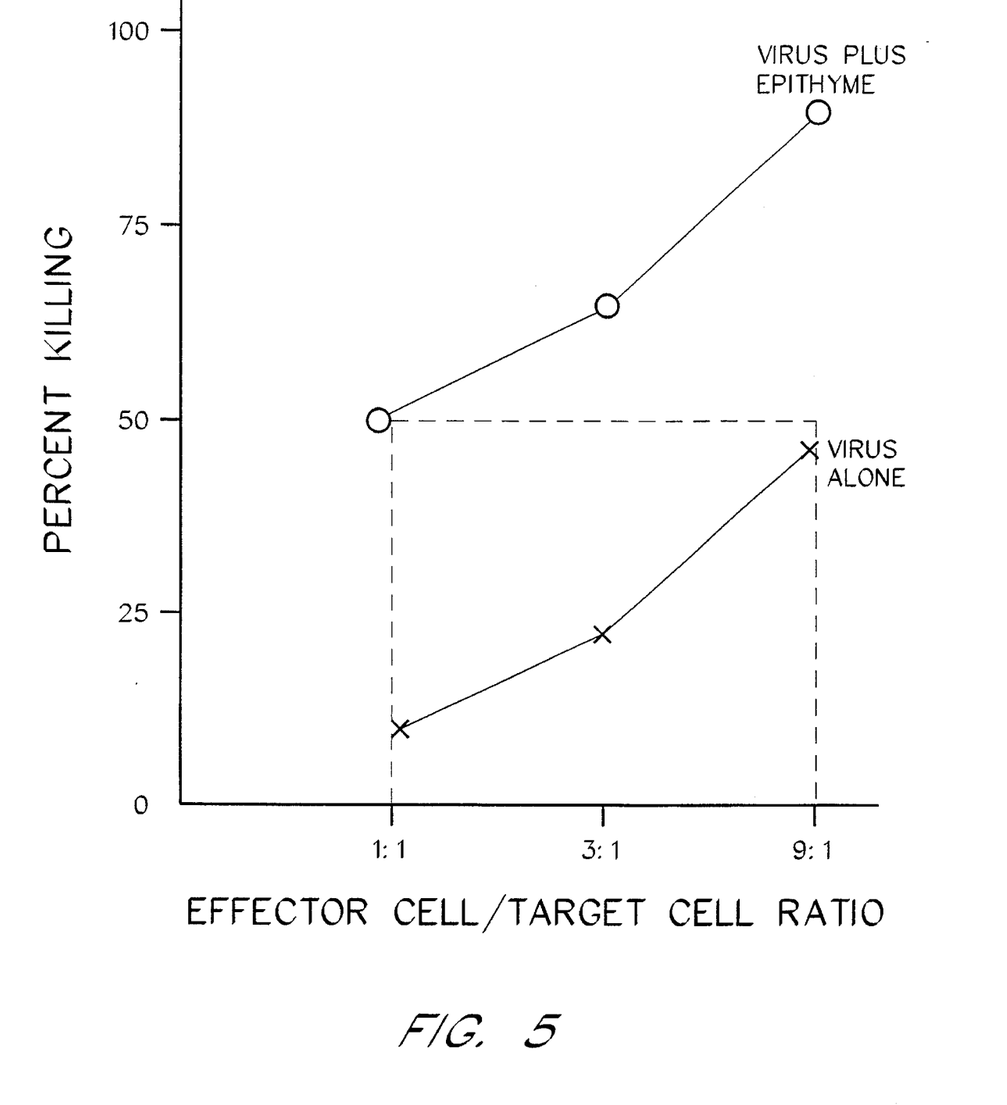
FIG. 5 illustrates the enhancement of killing activity via a test for secondary cytotoxic killer cell response against target cells infected with influenza virus.

In order to test this possibility, mice that had been infected with influenza plus or minus bovine TISF several weeks previously were tested for a secondary cytotoxic killer cell response against target cells infected with influenza virus. FIG. 5 illustrates secondary CMI response to influenza. The killing activity as measured by target cell lysis was enhanced at least 9-fold with lymphocytes from the TISF recipients.

EXAMPLE IV

Clinical Protocol

TISF has been demonstrated herein to enhance immune reactivity or responsiveness to several viral diseases. Weekly or twice-weekly administrations of TISF are expected to improve the immune status of felines infected with FIV.

Eleven cats ranging in age from one to three years were obtained from Dr. Janet Yamamoto at the University of California at Davis. The cats were experimentally infected with the Petaluma strain of FIV as controls in a vaccine trial. (See Pedersen, et al., *Science* 235: 790–93 (1987), which is incorporated herein by reference.)

All cats were determined to be FIV positive by Dr. Yamamoto but manifested no disease symptoms upon arrival at the test facility. The basic testing protocol is as follows:

1. Allow felines to rest and acclimate for about two weeks.
2. Obtain blood samples prior to initiation of treatment for baseline determination of lymphocyte counts and/or T4/T8 ratios.
3. Randomly assign felines to treatment (6 cats) or control (5 cats) groups.
4. Inject treatment group felines subcutaneously with 1.0 ml feline TISF in purified or semipurified form.
5. Obtain blood samples on a weekly basis prior to each injection. Monitor clinical signs and record findings.
6. Obtain bone marrow and/or blood sample for use in FIV detection test in treatment and control animals (e.g., appropriate staining of blood smears).

Figure 6:
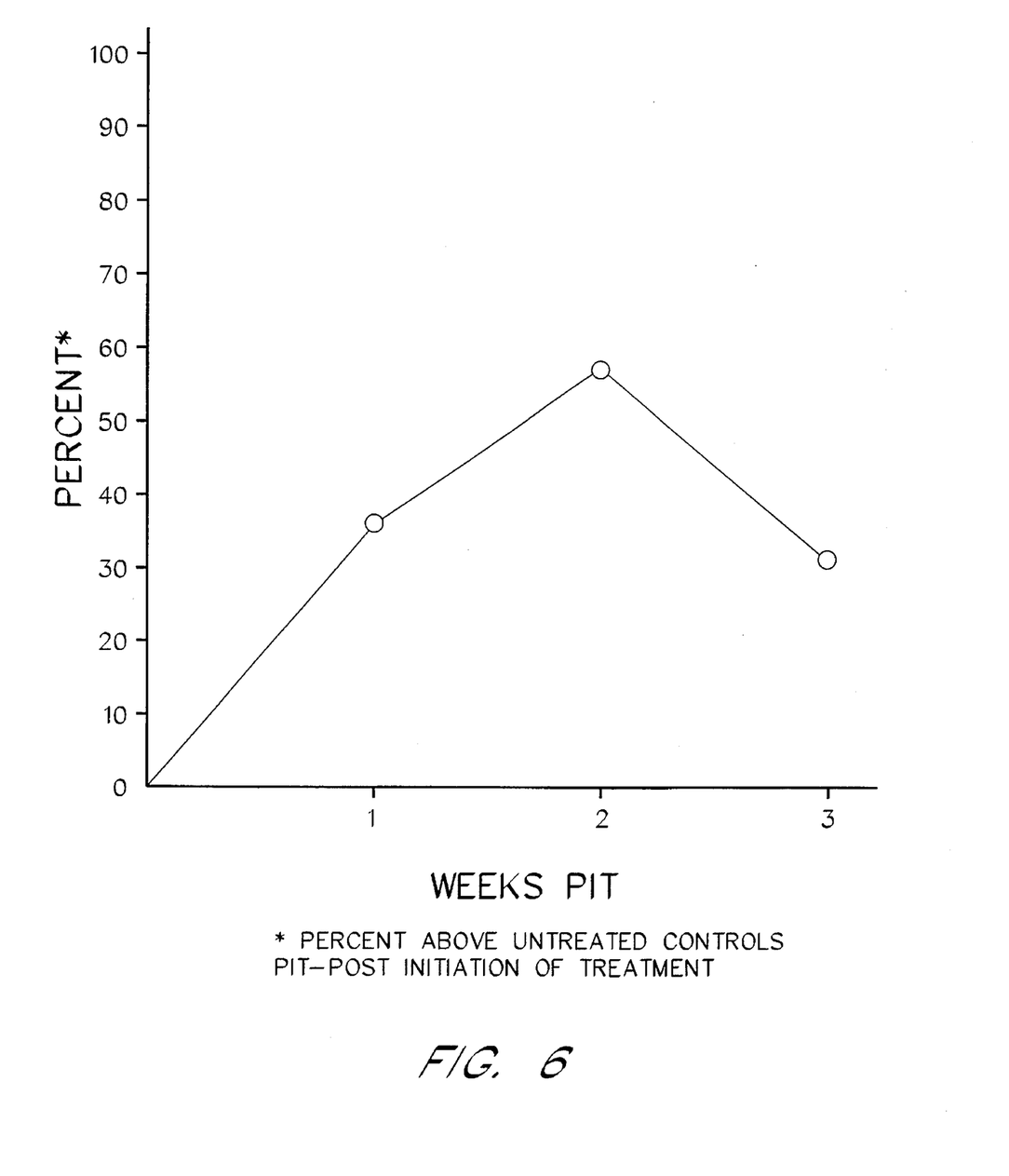
FIG. 6 illustrates the effect of TISF in cats infected with Feline Immunodeficiency Virus.

The six cats treated with TISF showed a statistically significant lessening of the period of lymphopenia encountered early in the course of FIV disease when compared to the five untreated controls (FIG. 6). Clinically, the experimentally treated group recovered much more rapidly from the signs of viral upper respiratory infections that were exhibited by all eleven animals. Finally, examination of blood and bone marrow from the animals confirmed that the group experimentally treated with TISF had improved virologic status and marrow cellularity when compared with controls.

EXAMPLE V

The following Table IV illustrates the results of treating symptomatic FIV positive cats in several private veterinary clinics with 1 ml/week of the product of the present invention comprising TISF in an injectable carrier at a concentration of 3 units/ml. As seen from the data in the table, all eight cats showed symptomatic improvement as well as increased peripheral blood lymphocyte counts after treatment with TISF.

TABLE IV

| | | CLINICAL STUDIES | | | |
|---|---|---|---|---|---|
| | | BEFORE Rx | | AFTER Rx | |
| PATIENT | SYMPTOMS | LYMPHS | SYMPTOMS | LYMPHS |
| SH | severe gingivitis severe stomatitis cryptococcus titer 1:500 | 9% | much improved eating well crypto titer 1:200 | 17% |
| JH | lethargic nasal discharge crypto titer | 15% | no symptoms crypto titer neg. | 39% |
| RJ | mucoid diarrhea | 37% | increased energy and appetite mouth improved | ND |
| DH | diarrhea sneezing | 19% | eating well normal appearance | 25% |

TABLE IV-continued

CLINICAL STUDIES

| | BEFORE Rx | | AFTER Rx | |
|---|---|---|---|---|
| PATIENT | SYMPTOMS | LYMPHS | SYMPTOMS | LYMPHS |
| BH | anorexic conjunctivitis | 18% | appetite improved improved appearance | 28% |
| AK | anorexic lymphadenopathy lethargic & depressed eating well | 4% | strong, doing better appearance improved | 21% |
| JN | weight loss respiratory infection swollen joints (abs. 2016/mm$^3$) | 24% | feeling better doing o.k. (abs. 4536/mm$^3$) | 25% |
| MH | very ill, weak respiratory infection weight loss | 0% | much improved infection resolved gained weight | 9% |

EXAMPLE VI

TISF produced by bovine thymic epithelial cells was tested for antiviral activity against the Human Immunodeficiency Virus (HIV). Human peripheral blood lymphocytes used for this in vitro test were obtained from healthy HIV-negative donors and were purified using discontinuous gradient centrifugation and Lymphocyte Separation Medium (Organon Teknika). The lymphocytes were stimulated initially with phytohemagglutinin (PHA) and were then maintained in a medium of RPMI-1640 and DMEM. Cells from this culture were concentrated and suspended in an inoculum of a known HIV strain (H112-2) for two hours. The cells were then washed to remove unabsorbed virus and were resuspended in fresh medium. $2 \times 10^5$ cells were dispensed into wells of a 24-well plate. Various concentrations of bovine TISF in two-fold dilutions from 1:5 to 1:160 were added to wells containing infected cells and to control wells containing uninfected cells.

Interleukin-2 (IL-2), in concentrations that varied between different plates, was added to the medium to assess the effect of varied lymphocyte stimulation levels. Cell controls (untreated, uninfected) and viral controls (untreated, infected) were included on each plate. Dideoxyinosine (DDI), a known powerful anti-HIV agent, was assayed as a positive control. The plates were cultured for 5 days at 37° C. in a humidified 5% $CO_2$ atmosphere. On the fifth or sixth day post-infection, a sample of the supernatant medium from each test well was collected and tested for HIV p24 core antigen concentration using an ELISA (Dupont Company, Boston, Mass.). The results of these determinations shown as the percent reduction in p24 antigen concentration compared with untreated viral controls are shown in Table V.

TABLE V

ANTIVIRAL ACTIVITY OF TISF IN THE PRESENCE OF IL-2

| | 1.0 u/ml Antiviral Activity | | .32 u/ml Antiviral Activity | | 0.1 u/ml Antiviral Activity | |
|---|---|---|---|---|---|---|
| IL-2 DOSAGE | p24 (ng/ml) | Reduction (%) | p24 (ng/ml) | Reduction (%) | p24 (ng/ml) | Reduction (%) |
| TISF 1:5 | 432.9 | 27.8 | 247.3 | 33.6 | 90.13 | 46.9 |
| TISF 1:10 | 517.3 | 13.7 | 292.4 | 21.5 | 92.93 | 45.2 |
| TISF 1:20 | 531.9 | 11.3 | 307.2 | 17.6 | 98.96 | 41.7 |
| TISF 1:40 | 579.3 | 3.4 | 313.7 | 15.8 | 111.6 | 34.2 |
| TISF 1:80 | 571.2 | 4.7 | 287.2 | 22.9 | 103.7 | 38.9 |
| TISF 1:160 | 602.2 | −0.4 | 309.6 | 16.9 | 115.5 | 31.9 |
| VIRAL CONTROL | 599.6 | — | 372.6 | — | 169.6 | — |
| DDI 100 μM | 0.312 | 99.96 | ND+ | — | ND | — |
| DDI 31.6 μM | 4.431 | 99.4 | ND | — | ND | — |
| DDI 10 μM | 158.8 | 79.0 | ND | — | ND | — |
| DDI 3.16 μM | 406.4 | 46.2 | ND | — | ND | — |
| DDI 1 μM | 529.1 | 30.0 | ND | — | ND | — |
| DDI .316 μM | 551.7 | 27.0 | ND | — | ND | — |
| VIRAL CONTROL | 755.6 | — | ND | — | ND | — |

*HIV p24 core antigen measured by ELISA
+ND = not determined

The effect of TISF on cell growth was assessed to verify that the viral inhibition it produced was not merely a reflection of cytotoxicity against the infected cells themselves, rather than an antiviral effect. A MTT-formazan dye assay was used to identify and quantify viable cells from uninfected wells at each dose dilution of TISF. This assay relies on the reduction by living cells of an MTT tetrazolium salt to form a blue formazan product. As shown in Table VI, while some cytotoxicity was seen at high TISF doses in cells under high IL-2 stimulation, at the lower concentrations and lower IL-2 levels more achievable in therapeutic situations, significant viral inhibition was noted even in the presence of increased cell growth.

TABLE VI

EFFECT OF TISF ON CELL GROWTH IN THE PRESENCE OF IL-2

| IL-2 DOSAGE | 1.0 u/ml Cell Viability | | .32 u/ml Cell Viability | | 0.1 u/ml Cell Viability | |
|---|---|---|---|---|---|---|
| | MTT Abs | (%) Cell Growth | MTT Abs | (%) Cell Growth | MTT Abs | (%) Cell Growth |
| TISF 1:5 | 0.994 | 92.6 | 0.761 | 85.1 | 0.371 | 81.7 |
| TISF 1:10 | 1.029 | 95.8 | 0.818 | 91.5 | 0.433 | 95.4 |
| TISF 1:20 | 1.059 | 98.6 | 0.828 | 92.6 | 0.457 | 102.9 |
| TISF 1:40 | 1.085 | 101.0 | 0.866 | 96.9 | 0.508 | 111.9 |
| TISF 1:80 | 1.07 | 99.6 | 0.872 | 97.5 | 0.541 | 119.2 |
| TISF 1:160 | 1.129 | 105.1 | 0.889 | 99.4 | 0.544 | 119.8 |
| CELL CONTROL | 1.074 | 100.0 | 0.894 | 100.0 | 0.454 | 100.0 |
| DDI 100 μM | 0.885 | 74.9 | ND+ | — | ND | — |
| DDI 31.6 μM | 1.096 | 92.7 | ND | — | ND | — |
| DDI 10 μM | 1.067 | 90.3 | ND | — | ND | — |
| DDI 3.16 μM | 1.077 | 91.1 | ND | — | ND | — |
| DDI 1 μM | 1.1 | 93.3 | ND | — | ND | — |
| DDI .316 μM | 1.169 | 98.9 | ND | — | ND | — |
| CELL CONTROL | 1.182 | 100.0 | ND | — | ND | — |

*MTT formazan absorption by living cells
+ND = not determined

This study demonstrated a striking reduction in the viral load of HIV-infected human lymphocytes caused by TISF that was not due merely to a cytotoxic effect. While the antiviral effect of TISF was less potent than that of DDI, TISF maintained its viral inhibition even under conditions where it also stimulated an increase in lymphocyte numbers. The foregoing detailed description of the invention and the preferred embodiments, especially with respect to product compositions and processes, is to be considered illustrative of specific embodiments only. It is to be understood, however, that additional embodiments may be perceived by those skilled in the art. The embodiments described herein, together with those additional embodiments, are considered to be well within the scope of the present invention.

What is claimed is:

1. An isolated thymus-derived cationic protein factor TISF expressed by a cloned type II thymic epithelial cell line of human, bovine, canine or feline origin, having a molecular weight of about 50,000 Daltons on a polyacrylamide gel, an isoelectric point of about 6.5, and capable of inducing or enhancing cell-mediated immune responsiveness of mature T-cells and stimulating IL-2 production in a mammal.

2. The factor of claim 1, of feline origin.

3. The factor of claim 1, of canine origin.

4. The factor of claim 1, of bovine origin.

5. The factor of claim 1, of human origin.

6. The factor according to claim 1, wherein said factor has the ability to enhance the response of a mammal to infection agents.

7. A composition comprising an effective, immune-responsiveness-enhancing amount of thymus-derived factor according to claim 1 incorporated in a pharmaceutically acceptable carrier or excipient.

8. A composition according to claim 7, in a form suitable for parenteral administration.

9. A composition according to claim 7, in a form suitable for intraperitoneal administration.

10. A composition according to claim 7, in a form suitable for topical administration.

11. A composition according to claim 7, in a form suitable for oral administration.

12. A method for enhancing immune responsiveness of a mammal against a virus selected from the group consisting of Feline Immunodeficiency Virus, rabies virus, influenza virus, and distemper virus, comprising administering to said, mammal an effective immune response-enhancing amount of the factor of claim 1.

13. A method for enhancing immune responsiveness of a mammal against a virus selected from the group consisting of Feline Immunodeficiency Virus, rabies virus, influenza virus, and distemper virus, comprising administering to said mammal an effective immune response-enhancing amount of the factor of claim 7.

14. A method according to claim 12, wherein said virus is Feline Immunodeficiency Virus.

15. A method according to claim 12, wherein said virus is rabies virus.

16. A method according to claim 12, wherein said virus is distemper virus.

17. The method of claim 12, wherein said mammal is a feline.

18. The method of claim 12, wherein said mammal is a canine.

19. The method of claim 12, wherein said mammal is a human.

20. The method of claim 18, wherein said factor is administered parenterally.

21. The method of claim 12, wherein said factor is administered intraperitoneally.

22. The method of claim 12, wherein said factor is administered after being incorporated within liposomes.

23. The method of claim 12, wherein said factor is administered topically.

24. The method of claim 12, wherein said factor is administered orally.

* * * * *

UNITED STATES PATENT AND TRADEMARK OFFICE
CERTIFICATE OF CORRECTION

| | | |
|---|---|---|
| PATENT NO. | : 5,616,554 | Page 1 of 1 |
| APPLICATION NO. | : 08/280781 | |
| DATED | : April 1, 1997 | |
| INVENTOR(S) | : Terry R. Beardsley | |

It is certified that error appears in the above-identified patent and that said Letters Patent is hereby corrected as shown below:

In the Claims

Column 15, line 57, in claim 6, delete "infection" and insert -- infectious --, therefor.

Column 16, line 33, in claim 12, after "said" delete ",".

Column 16, line 55, in claim 20, delete "claim 18" and insert -- claim 12 --, therefor.

Signed and Sealed this

Seventeenth Day of April, 2007

JON W. DUDAS
*Director of the United States Patent and Trademark Office*